US010435504B2

(12) United States Patent
Bae et al.

(10) Patent No.: US 10,435,504 B2
(45) Date of Patent: Oct. 8, 2019

(54) POLYMERS AND METHODS FOR THEIR MANUFACTURE (71) Applicant: Rensselaer Polytechnic Institute, Troy, NY (US)

(72) Inventors: Chulsung Bae, Cohoes, NY (US); Woo-hyung Lee, Siheung-Si (KR)

(73) Assignee: Rensselaer Polytechnic Institute, Troy, NY (US)

(*) Notice: Subject to any disclaimer, the term of this patent is extended or adjusted under 35 U.S.C. 154(b) by 0 days.

(21) Appl. No.: 15/527,967

(22) PCT Filed: Nov. 17, 2015

(86) PCT No.: PCT/US2015/061036
§ 371 (c)(1),
(2) Date: May 18, 2017

(87) PCT Pub. No.: WO2016/081432
PCT Pub. Date: May 26, 2016

(65) Prior Publication Data
US 2017/0355811 A1 Dec. 14, 2017

Related U.S. Application Data (60) Provisional application No. 62/081,144, filed on Nov. 18, 2014.

(51) Int. Cl.
C08G 61/02 (2006.01)
A01N 29/00 (2006.01)
H01M 8/1039 (2016.01)
H01M 8/1072 (2016.01)
C09D 5/14 (2006.01)
C09D 165/00 (2006.01)
(Continued)

(52) U.S. Cl.
CPC ............. *C08G 61/02* (2013.01); *A01N 29/00* (2013.01); *C08G 10/00* (2013.01); *C09D 5/14* (2013.01); *C09D 165/00* (2013.01); *C25B 13/08* (2013.01); *H01M 8/1004* (2013.01); *H01M 8/1039* (2013.01); *H01M 8/1072* (2013.01); *C08G 2261/124* (2013.01); *C08G 2261/146* (2013.01); *C08G 2261/20* (2013.01); *C08G 2261/312* (2013.01); *C08G 2261/332* (2013.01); *C08G 2261/45* (2013.01); *Y02P 70/56* (2015.11)

(58) Field of Classification Search
CPC ...................................................... C08G 61/02
USPC ......................................... 528/229, 228, 397
See application file for complete search history.

(56) References Cited

U.S. PATENT DOCUMENTS 7,615,300 B2    11/2009  Bae
2014/0024728 A1  1/2014  Kim et al.
2014/0275300 A1  9/2014  Kim et al.

OTHER PUBLICATIONS

Mohanty et al., "Anion Exchange Fuel Cell Membranes Prepared from C-H Borylation and Suzuki Coupling Reactions", Macromolecules, 2014, 47, p. 1973-1980.
(Continued)

*Primary Examiner* — Duc Truong
(74) *Attorney, Agent, or Firm* — Murtha Cullina LLP; Anthony P. Gangemi (57) ABSTRACT

Embodiments of the invention relate to a novel class of polymers with superior mechanical properties and chemical stability, as compared to known polymers. These polymers are particularly well suited for use in anion exchange membranes (AEMs), including those employed in fuel cells. Novel methods for the manufacture of these polymers are also described.

16 Claims, 5 Drawing Sheets

(51) Int. Cl.
*C25B 13/08* (2006.01)
*H01M 8/1004* (2016.01)
*C08G 10/00* (2006.01)

(56) References Cited

OTHER PUBLICATIONS

International Search Report and Written Opinion for International Application No. PCT/US2015/061036, dated Feb. 4, 2016, 7 pages.

POLYMERS AND METHODS FOR THEIR MANUFACTURE

CROSS-REFERENCE TO RELATED APPLICATIONS

This application claims the benefit of U.S. Provisional Patent Application Ser. No. 62/081,144, filed 18 Nov. 2014, which is hereby incorporated herein as though fully set forth.

BACKGROUND

Alkaline exchange membranes or anion exchange membranes (AEMs) allow for the transportation of anions (e.g., $OH^-$, $Cl^-$, $Br^-$) from the cathode to the anode in an electrochemical reaction. AEMs are a critical component of AEM fuel cells, where hydrogen and oxygen are used to generate electricity, with water as a byproduct. AEMs are also used in water electrolysis, where water is split into hydrogen and oxygen using electricity. In both AEM fuel cells and water electrolysis, hydroxide ions ($OH^-$) are transported through the AEM, along with water molecules. AEMs may also be used, for example, in batteries, sensors, and as actuators.

Known AEMs are generally unsuitable for use in AEM fuel cells or water electrolysis. Many commercially-available AEMs are based on polystyrene, which is generally considered a poor choice for AEM fuel cells or water electrolysis.

Other AEM materials include polysulfones, poly(phenylene oxide)s, poly(phenylene)s, poly(benzimidazolium)s, poly(arylene ether ketone)s, and poly(arylene ether sulfone) s. These polymers contain an arylene ether linkage (—O—) in the mid-chain and a benzyltrimethyl ammonium group in the side-chain. This combination, however, has been found to be chemically unstable and to degrade easily under highly alkaline conditions. Known polyarylenes, in particular, will contain ether linkages in the polymer backbone because they are typically synthesized by basic condensation reactions between diol monomers and dihalide monomers, which produces hydrogen chloride as a byproduct.

In addition, the chloromethylation reaction involved in the manufacture of these polymers requires the use of toxic reagents, long reaction times, and extensive optimization to reach a desired degree of functionalization. Side reactions (e.g., gelation) frequently occur over prolonged reaction times, making it difficult to achieve an ion-exchange capacity (IEC) above 2.5 mequiv/g.

BRIEF DESCRIPTION OF THE INVENTION

In one embodiment, the invention provides a method of forming a polymer, the method comprising: reacting an aromatic compound and a trifluoroalkyl ketone in the presence of a strong acid to form a bromoalkylated precursor polymer; and reacting the bromoalkylated precursor polymer with a trialkylamine and sodium hydroxide to form a polyarylene having a main chain free of ether linkages.

In another embodiment, the invention provides a polymer according to formula I (formula I), wherein Ar is an aromatic compound, r is from 100 to 1,000,000, $R^2$ is

R is an alkyl group, and n is from 1 to 20.

In still another embodiment, the invention provides polymer according to formula III (formula III)

wherein Ar is an aromatic compound, R" is r is from 100 to 1,000,000, and m is from 0 to 20.

BRIEF DESCRIPTION OF THE DRAWINGS

These and other features of this invention will be more readily understood from the following detailed description of the various aspects of the invention taken in conjunction with the accompanying drawings that depict various embodiments of the invention, in which.

It is noted that the drawings of the invention are not to scale. The drawings are intended to depict only typical aspects of the invention, and therefore should not be considered as limiting the scope of the invention.

DETAILED DESCRIPTION

Some embodiments of the invention relate to a novel class of quaternized ammonium hydroxide-containing polyarylene polymers and methods for their manufacture. Applicants have, for the first time, manufactured high molecular weight, quaternary ammonium-tethered polyarylenes (including poly(biphenyl alkylene)s) without alkaline labile C—O bonds using acid-catalyzed polycondensation reactions.

In addition to their use in AEMs in the fuel cell and water electrolysis contexts noted above, Applicants have also found polymers of the invention to be useful in metal-air battery technologies. Surprisingly, Applicants have also found that these polymers exhibit antimicrobial activity, making them potentially useful as antimicrobial coatings for any number of products.

As will be explained in greater detail below, the polymers of the invention are synthesized by acidic condensation between ketone and aromatic compounds. As a result, the byproduct is water, rather than hydrogen chloride, as in known polyarylene synthesis methods.

Applicants have developed a novel method of polymer manufacture, generally comprising: reacting an aromatic compound and a trifluoroalkyl ketone in the presence of a strong acid (acid-catalyzed Friedel-Crafts polycondensation) to form a bromoalkylated precursor polymer; and reacting the bromoalkylated precursor polymer with a trialkylamine in the presence of sodium hydroxide to form a polyarylene having a main chain free of ether linkages.

According to some embodiments of the invention, the aromatic compound is selected from a group consisting of:

,

,

,

,

,

, and

According to other embodiments of the invention, the aromatic compound is selected from a group consisting of:

,

,

,

,

.

In some particular embodiments of the invention, the aromatic compound is biphenyl.

According to some embodiments of the invention, the trifluoroalkyl ketone is selected from a group consisting of: 7-bromo-1,1,1-trifluoroheptan-2-one and methyl trifluoromethyl ketone.

According to some embodiments of the invention, a polymer is manufactured according to Reaction 1 below, where Ar is a polyarylene, r is from 100 to 1,000,000, $R^1$ is $R^2$ is R is an alkyl group, and n is from 1 to 20.

(Reaction 1)

-continued

Strong acids suitable for use in Reaction 1 include trifluoromethane sulfonic acid, although other suitable acids will be apparent to one of ordinary skill in the art.

In other embodiments of the invention, an aromatic group may be combined with multiple trifluoroalkyl ketones, as in Reaction 1A below, where Ar is an aromatic compound, r is from 100 to 1,000,000, $R^1$ is $R^2$ is

R is an alkyl group, and n is from 1 to 20.

(Reaction 1A)

The manufacture of three exemplary poly(biphenyl alkylene)s according to embodiments of the invention is described below. These poly(biphenyl alkylene)s have general formula IA (formula 1A)

where $R^2$ is $x+y=1$, and r is from 100 to 1,000,000. In a first poly(biphenyl alkylene), referred to as PBPA+, x is 1 and y is 0. In a second poly(biphenyl alkylene), referred to as PBPA1+, x is 0.65 and y is 0.35. In a third poly(biphenyl alkylene), referred to as PBPA2+, x is 0.44 and y is 0.56.

Example 1—PBPA+

Figure 1:
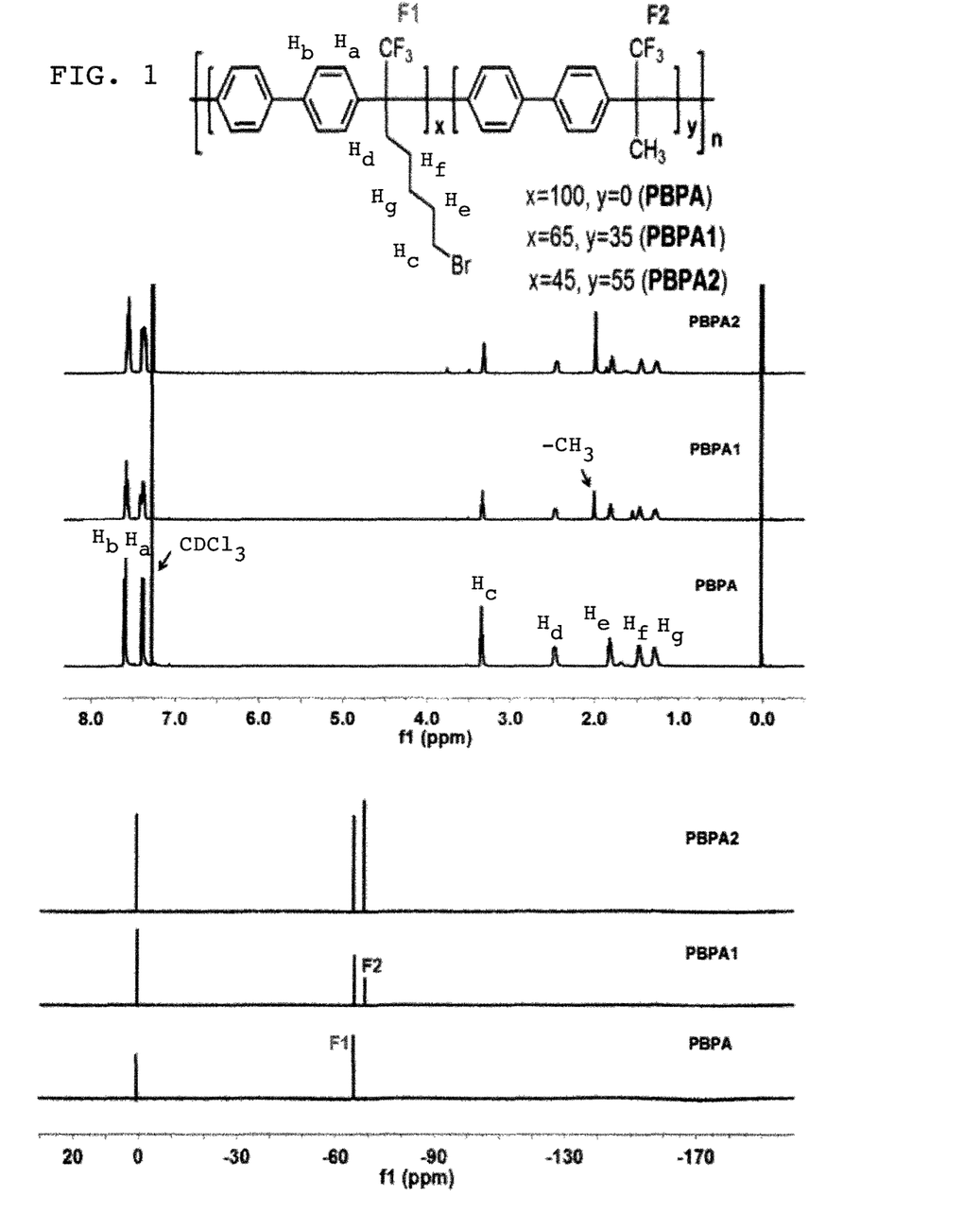
FIG. 1 shows $^1H$ and $^{19}F$ NMR spectra of three illustrative bromoalkylated precursor polymers according to embodiments of the invention.

Biphenyl (0.70 g, 4.53 mmol), 7-bromo-1,1,1-trifluoroheptan-2-one (1.12 g, 4.53 mmol), methylene chloride (3.0 mL), and trifluoromethanesulfonic acid (TFSA) were mixed under nitrogen at room temperature using a magnetic stirring bar. After 10 hours, the reaction mixture solution became highly viscous and was stirred for an additional two hours. The resulting dark brown, gel-like mass was then shredded with sonication and poured slowly into methanol, forming a white fiber, which was then filtered and washed with hot methanol. After vacuum drying, 1.70 g (97% yield) of a white fiber-like solid, a bromoalkylated precursor polymer referred to herein as PBPA, was obtained. FIG. 1 shows $^1$H and $^{19}$F NMR spectra of three bromoalkylated poly(biphenyl alkylene) precursors, including PBPA.

Figure 2:
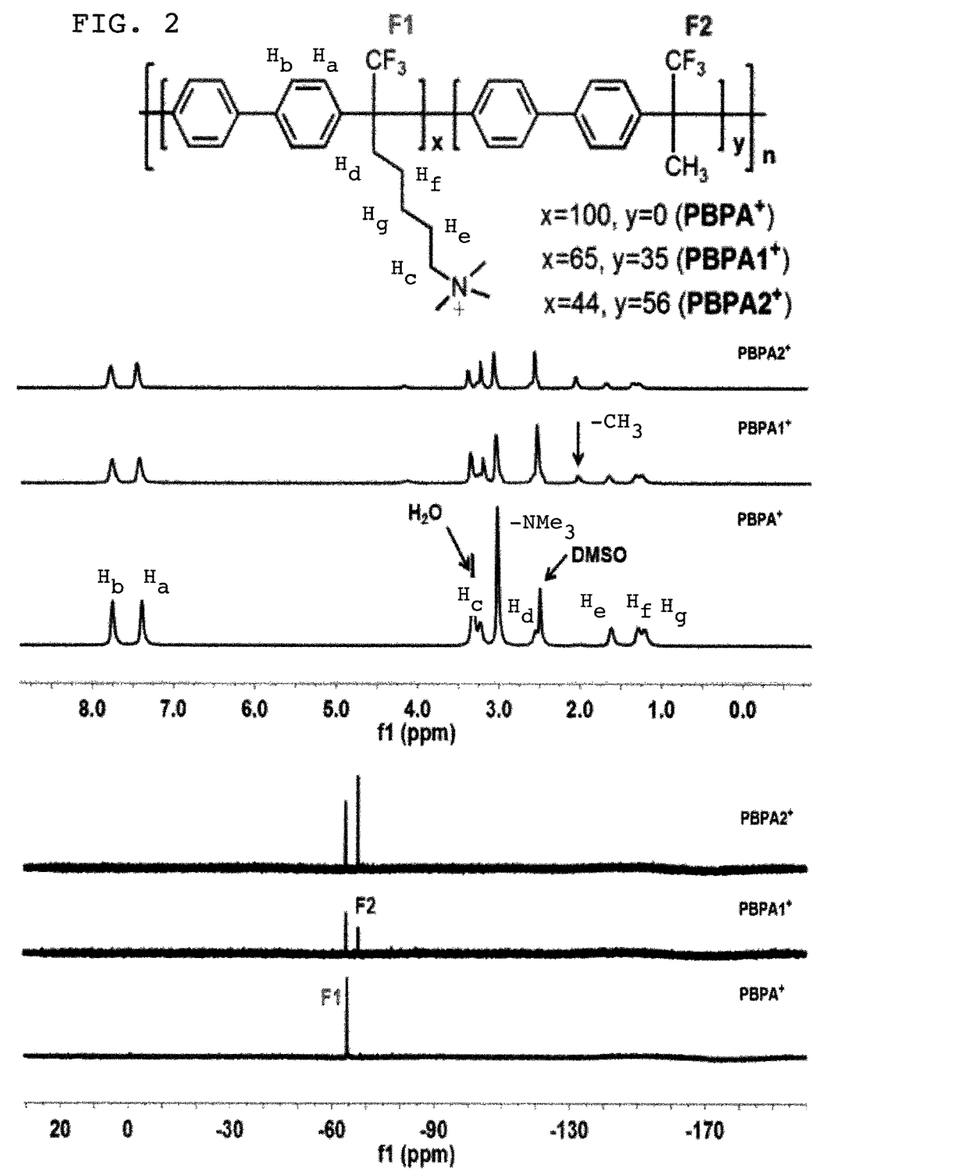
FIG. 2 shows $^1H$ and $^{19}F$ NMR spectra of three illustrative polyarylenes according to embodiments of the invention.

PBPA (200 mg) was dissolved in tetrahydrofuran (THF; 2 mL) and aqueous trimethylamine (1 mL) added to the solution, which was stirred at room temperature. The solubility of the polymer gradually decreased and the ionic polymer was precipitated after six hours. Deionized water (1 mL) was added to the solution to dissolve the precipitate. Addition of THF, stirring at RT for six hours, and dissolution with deionized water was repeated. Volatile solven was then evaporated using a rotary evaporator and the residue redissolved with a small amount of methanol (approximately 2 mL). The ionic polymer was precipitated by adding ether, filtered, and dried under vacuum, resulting in a 97% yield (227 mg) of the poly(biphenyl alkylene) PBPA+. FIG. 2 shows $^1$H and $^{19}$F NMR spectra of three poly(biphenyl alkylene)s, including PBPA+.

Example 2—PBPA1+

Biphenyl (0.70 g, 4.53 mmol), 7-bromo-1,1,1-trifluoroheptan-2-one (0.73 g, 2.95 mmol), methyl trifluoromethyl ketone (0.18 g, 1.60 mmol), methylene chloride (3.0 mL), and TFSA (2.0 mL) were stirred under nitrogen at RT using a magnetic stirring bar. After five hours, the reaction mixture solution became highly viscous and was stirred for an additional two hours. The resulting dark brown, gel-like mass was then shredded with sonication and poured slowly into methanol. A white fiber formed and was filtered and washed with hot methanol. After drying under vacuum, 1.4 g (96% yield) solid, a bromoalkylated precursor polymer referred to herein as PBPA1, was obtained. FIG. 1 shows $^1$H and $^{19}$F NMR spectra of three bromoalkylated poly(biphenyl alkylene) precursors, including PBPA1.

PBPA1 (200 mg) was dissolved in tetrahydrofuran (THF; 2 mL) and aqueous trimethylamine (1 mL) added to the solution, which was stirred at room temperature. The solubility of the polymer gradually decreased and the ionic polymer was precipitated after six hours. Deionized water (1 mL) was added to the solution to dissolve the precipitate. Addition of THF, stirring at RT for six hours, and dissolution with deionized water was repeated. Volatile solven was then evaporated using a rotary evaporator and the residue redissolved with a small amount of methanol (approximately 2 mL). The ionic polymer was precipitated by adding ether, filtered, and dried under vacuum, resulting in a 98% yield (219 mg) of the poly(biphenyl alkylene) PBPA1+. FIG. 2 shows $^1$H and $^{19}$F NMR spectra of three poly(biphenyl alkylene)s, including PBPA1+.

Example 3—PBPA2+

Biphenyl (0.50 g, 3.24 mmol), 7-bromo-1,1,1-trifluoro-heptan-2-one (0.40 g, 1.62 mmol), methyl trifluoromethyl ketone (0.19 g, 1.69 mmol), methylene chloride (2.5 mL), and TFSA (2.3 mL) were stirred under nitrogen at RT using a magnetic stirring bar. After three hours, the reaction mixture solution became highly viscous and was stirred an additional two hours. The resulting dark brown, gel-like mass was then shredded with sonication and poured slowly into methanol. A white fiber formed and was filtered and washed with hot methanol. After drying under vacuum, 0.94 g of a white fiber-like solid, a bromoalkylated precursor polymer referred to herein as PBPA2, was obtained. FIG. 1 shows $^1$H and $^{19}$F NMR spectra of three bromoalkylated poly(biphenyl alkylene) precursors, including PBPA2.

PBPA2 (200 mg) was dissolved in tetrahydrofuran (THF; 2 mL) and aqueous trimethylamine (1 mL) added to the solution, which was stirred at room temperature. The solubility of the polymer gradually decreased and the ionic polymer was precipitated after six hours. Deionized water (1 mL) was added to the solution to dissolve the precipitate. Addition of THF, stirring at RT for six hours, and dissolution with deionized water was repeated. Volatile solvent was then evaporated using a rotary evaporator and the residue redissolved with a small amount of methanol (approximately 2 mL). The ionic polymer was precipitated by adding ether, filtered, and dried under vacuum, resulting in a 98% yield (210 mg) of the poly(biphenyl alkylene) PBPA2+. FIG. 2 shows $^1$H and $^{19}$F NMR spectra of three poly(biphenyl alkylene)s, including PBPA2+.

Table 1 below shows water uptake (WU) and anion conductivity data for the PBPA+, PBPA1+, and PBPA2+ polymers.

| Ionic polymer | WU(%) 30° C. | WU(%) 80° C. | Cl$^-$ (mS/cm) 30° C. | Cl$^-$ (mS/cm) 60° C. | Cl$^-$ (mS/cm) 80° C. | OH$^-$ (mS/cm) 30° C. | OH$^-$ (mS/cm) 60° C. | OH$^-$ (mS/cm) 80° C. |
|---|---|---|---|---|---|---|---|---|
| PBPA$^+$ | 130 | 145 | 23 | 49 | 68/65$^a$ | 62 | 94 | 122/124$^a$ |
| PBPA1$^+$ | 102 | 110 | 14 | 28 | 47/50$^a$ | 41 | 58 | 88/92$^a$ |
| PBPA2$^+$ | 70 | 76 | 7 | 14 | 24/22$^a$ | 25 | 23 | 35/35$^a$ |

$^a$After immersion to 1M NaOH solution for 30 days.

All three polymers exhibited excellent WU and conductivity properties, particularly PBPA+. Despite these WU values, all three polymers exhibited low swelling ratios (40% for PBPA+, 10% for PBPA1+, and 5% for PBPA2+), likely due to the presence of a rigid aromatic backbone.

Table 2 below shows ion-exchange capacity (IEC) data in mequiv/g for the PBPA+, PBPA1+, and PBPA2+ polymers before and after alkaline stability testing.

| Sample | before $^1$H NMR | before titration | After 80° C., 7 day $^1$H NMR | After 80° C., 7 day titration | After 80° C., 30 day $^1$H NMR | After 80° C., 30 day titration |
|---|---|---|---|---|---|---|
| PBPA$^+$ | 2.61 | 3.70 (±0.1) | 2.61 | 2.74 (±0.1) | 2.60 | 2.65 (±0.03) |
| PBPA1$^+$ | 1.91 | 1.94 (±0.04) | 1.89 | 1.94 (±0.03) | 1.93 | 1.92 (±0.03) |
| PBPA2$^+$ | 1.45 | 1.46 (±0.01) | 1.49 | 1.47 (±0.03) | 1.46 | 1.48 (±0.01) |

As can be seen from the data in Table 2, all three poly(biphenyl alkylene)s exhibited remarkable IEC stability in an alkaline environment (1M NaOH), even after an extended period. As should also be apparent from the results in Table 2 and the examples above, the IEC of the polymers may be controlled by adjusting the relative proportions of different trifluoroalkyl ketones.

Interestingly, PBPA1+ afforded significantly higher hydroxide ion conductivity than other reported aromatic AEMs with similar IECs (e.g., quaternized poly(phenylene oxide)s, poly(arylene ether ketone)s, and poly(arylene ether sulfone)s). This is likely attributable to the relatively higher WU of PBPA1+, which helps the hydrated membrane diffuse hydroxide ions more effectively. All three polymers exhibit increased hydroxide ion conductivity with increasing temperature, primarily due to the faster migration of ions and higher diffusivity with increasing temperature.

Figure 3:
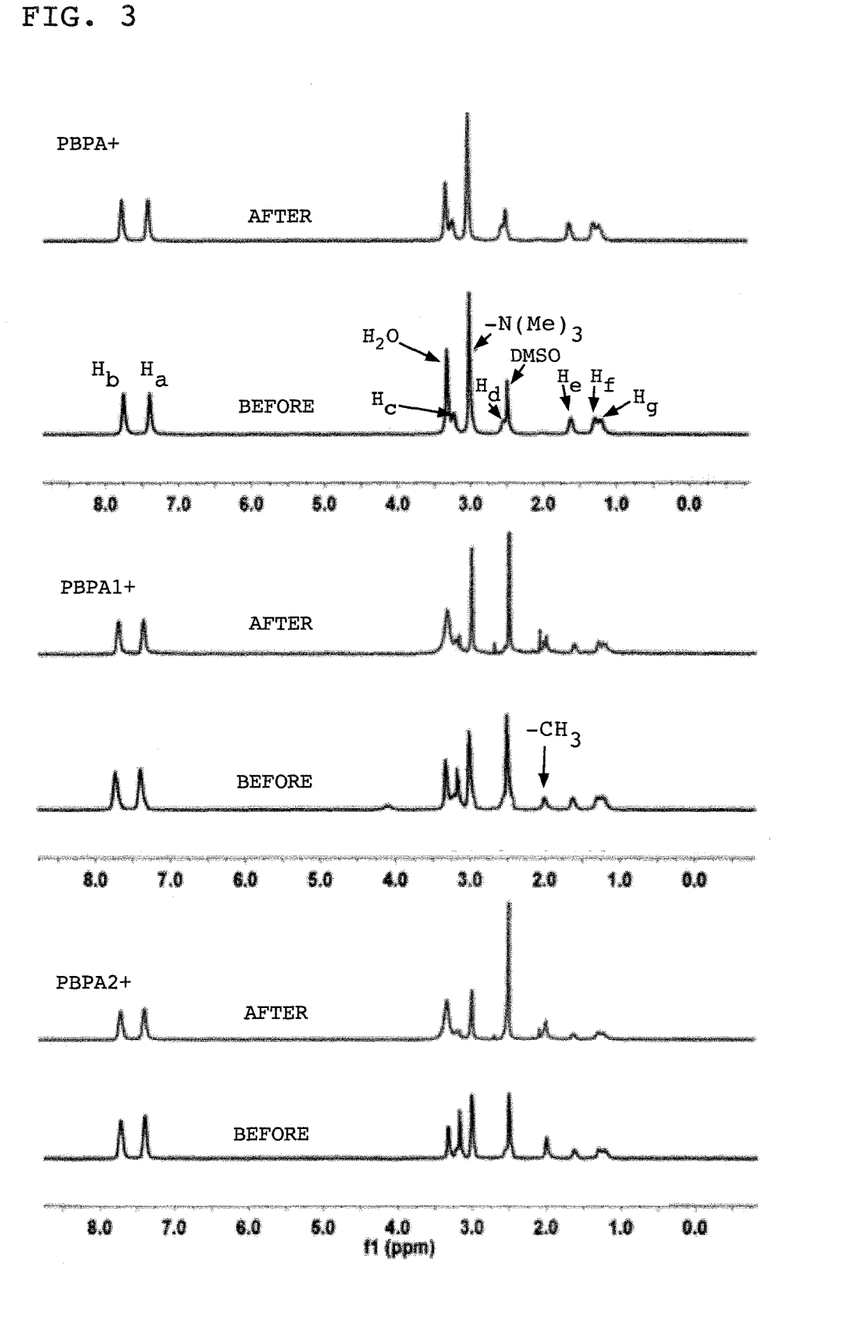
FIG. 3 shows $^1H$ NMR spectra of the three polyarylenes of FIG. 2 before and after alkaline stability tests.
Figure 4:
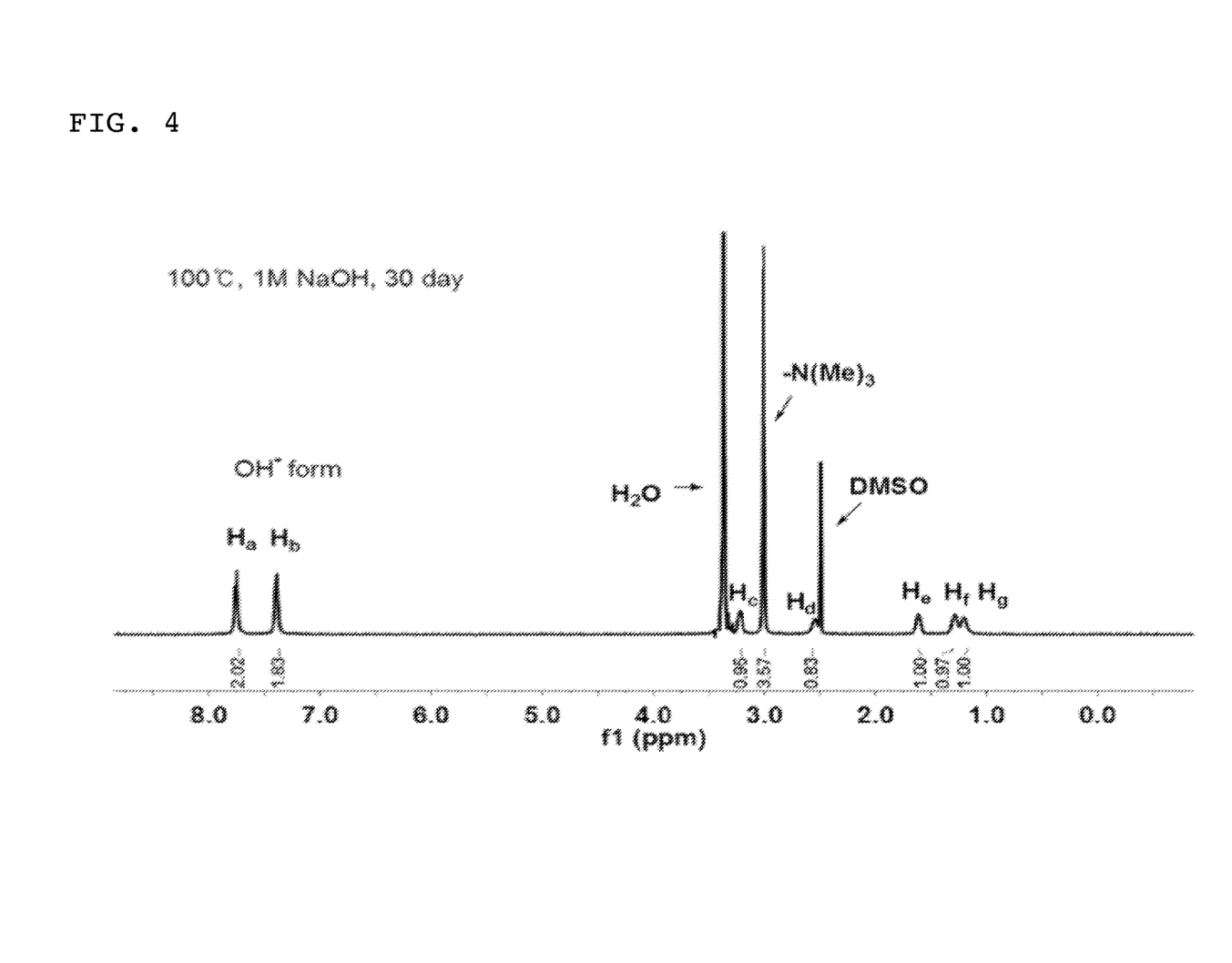
FIG. 4 shows a $^1H$ NMR spectrum of one of the three polyarylenes of FIG. 2 before and after an alkaline stability test.

FIG. 3 shows $^1$H NMR spectra for PBPA+, PBPA1+, and PBPA2+ before and after the 30-day alkaline stability test (1M NaOH, 80° C.) described above in Table 2. FIG. 4 shows $^1$H NMR spectra data for PBPA+ following another alkaline test (1M NaOH, 100° C., 30 days).

PBPA+, PBPA1+, and PBPA2+ are insoluble in water, tetrahydrofuran, trichloromethane ($CHCl_3$), and dichloroethene ($CH_2Cl_2$), but are soluble in N,N-dimethylformamide, dimethylsulfoxide, and methanol at room temperature. The quaternary ammonium groups of these polymers decomposed at 270° C., a thermal stability greater than that reported for QA poly(arylene ether sulfone)s. The precursor polymers (PBPA, PBPA1, PBPA2) were thermally stable without decomposition up to 350° C.

The mechanical properties of AEMs are critically important in fuel cell applications. For each of the PBPA+, PBPA1+, and PBPA2+ polymers, the tensile strength and elongation at the break of the membranes were, respectively, 20-35 MPa and 40-140%, which meet the requirements for building membrane electrode assemblies (MEAs) in AEM fuel cells.

Figure 5:
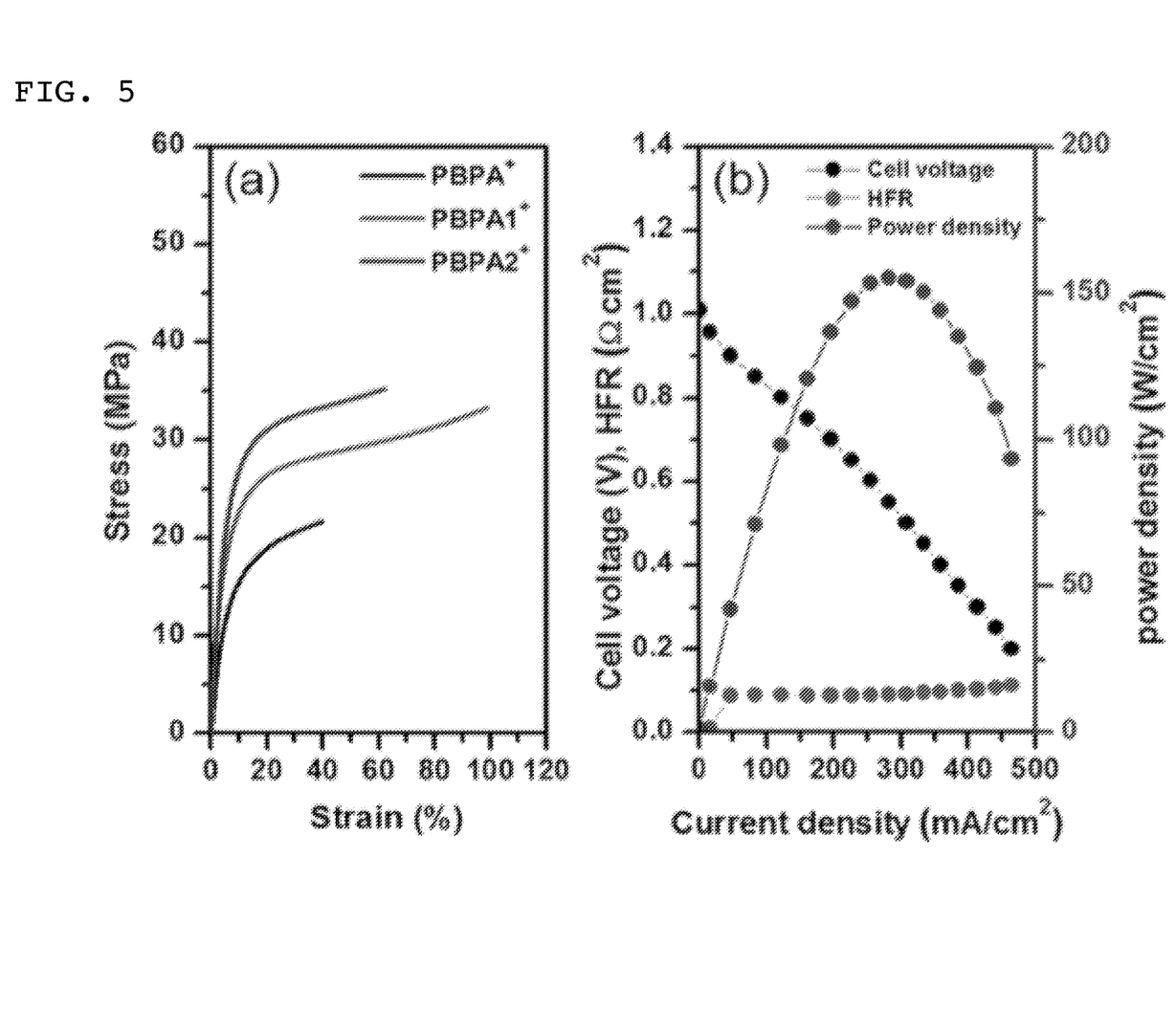
FIG. 5 shows (a) stress and strain curves of three polyarylenes according to embodiments of the invention and (b) $H_2/O_2$ polarization, high-frequency resistance, and power density curves of one of the three polyarylenes.

FIG. 5 show stress versus strain curves (panel (a)) for all three polymers. At 50° C. and 50% relative humidity, membranes comprising the polymer with the lowest IEC (PBPA2+) had a mechanical strength (35 MPa) greater than that of a membrane comprising PBPA+ (22 MPa), the polymer with the highest IEC. And compared to Diels-Alder poly(phenylene) AEMs (IEC=1.7 mequiv/g, 32 MPa maximum strength, 40% maximum strain), membranes comprising the PBPA1+ polymer showed similar tensile strength (IEC=1.9 mequiv/g, 33 MPa maximum strength, 100% maximum strain) but significantly better elongation at break, likely due to its more flexible backbone structure having a quaternary spa carbon. These mechanical strength data indicate that the polymers of the invention are tough and ductile enough for use as AEM materials in fuel cells.

Panel (b) of FIG. 5 shows the polarization curves of fuel cells containing PBPA1+ at 80° C. The open-circuit voltage (OCV) was 1.01 V, which is typical in hydrogen-supplied fuel cells. The maximum power density of 155 mW/cm$^2$ was obtained at 80° C. and the high-frequency resistance (HFR) of the cell was <0.1 Ωcm$^2$. While the membrane conductivity obtained from the HFR is 19.9 S/cm, lower than the value from the ex situ measurement due to the nonmembrane resistance contributions of the MEA, the HFR value reported here was much smaller than typical values found in literature reports of AEM fuel cells.

These results clearly demonstrate the superior chemical stability and fuel cell performance of QA poly(biphenyl alkylene)s according to the invention, as compared to other AEM materials.

Polyarylenes other than the poly(biphenyl alkylene)s described above are within the scope of the invention and may be manufactured according to similar methods. For example, methods of the invention may be employed to manufacture a polymer according to formula III

(formula III)

wherein Ar is an aromatic compound, R" is r is from 100 to 1,000,000, and m is from 0 to 20.

According to some embodiments of the invention, polymers of formula III may be manufactured according to Reaction 2 below, wherein Ar is a polyarylene, R' is m is from 0 to 20, r is from 100 to 1,000,000, R is an aryl group, and R" is

(Reaction 2)

According to some embodiments of the invention, the aromatic compound is selected from a group consisting of:

Other aromatic compounds may be employed, of course, as will be recognized by one skilled in the art and are within the scope of the invention. Similarly, in some embodiments, is methyl trifluoromethyl ketone. Other trifluoroalky ketones will be apparent to one skilled in the art and are within the scope of the invention.

Finally, although the embodiments above include brominated aromatic compounds or trifluoroalkyl ketones, other halogens may be employed. For example, 7-chloro-1,1,1-trifluoroheptan-2-one could be employed to prepare a chloroalkylated precursor polymer, from which polymers according to the invention are prepared through nucleophilic substitution. In such embodiments, groups other than ammonium groups (e.g., alkyloxy, sulfonate, carboxylate, phosphonate) may be included in the resulting polymer.

As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

This written description uses examples to disclose the invention, including the best mode, and also to enable any person skilled in the art to practice the invention, including making and using any devices or systems and performing any related or incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of forming a polyarylene, the method comprising: reacting an aromatic compound and a trifluoroalkyl ketone in the presence of a strong acid to form a bromoalkylated precursor polymer; and reacting the bromoalkylated precursor polymer with a trialkylamine and sodium hydroxide to form a polyarylene having a main chain free of ether linkages.

2. The method of claim 1, wherein the trifluoroalkyl ketone includes at least one trifuloroalkyl ketone selected from a group consisting of: 7-bromo-1,1,1-trifluoroheptan-2-one and methyl trifluoromethyl ketone.

3. The method of claim 1, wherein the aromatic compound is selected from a group consisting of:

4. The method of claim 3, wherein the aromatic compound is

5. The method of claim 1, wherein the aromatic compound is selected from a group consisting of:

, and

6. A polymer of formula I prepared according to the method of claim 1

(formula I)

wherein Ar is an aromatic compound, r is from 100 to 1,000,000, $R^2$ is

R is an alkyl group, and n is from 1 to 20.

7. The polymer of claim 6, wherein Ar is

8. The polymer of claim 7 having formula IA wherein x+y=1.

9. The polymer of claim 8, wherein x is 1 and y is 0, or x is 0.65 and y is 0.35, or x is 0.44 and y is 0.56.

10. A polymer according to formula I

(formula I)

wherein Ar is an aromatic compound, r is from 100 to 1,000,000, $R^2$ is R is an alkyl group, and n is from 1 to 20.

11. The polymer of claim 10, wherein the aromatic compound is selected from a group consisting of:

, and

12. The polymer of claim 10, prepared from a bromoalkylated precursor polymer of formula II according to the reaction:

wherein $R^1$ is

13. The polymer of claim 10, wherein the bromoalkylated precursor polymer of formula II is prepared according to the reaction:

(formula II)

14. The polymer of claim 13, wherein the strong acid is trifluoromethanesulfonic acid.

15. The polymer of claim 10 having formula IA wherein x+y=1.

16. The polymer of claim 15, wherein x is 1 and y is 0, or x is 0.65 and y is 0.35, or x is 0.44 and y is 0.56.

* * * * *